United States Patent [19]

Pederson

[11] Patent Number: 4,628,558
[45] Date of Patent: Dec. 16, 1986

[54] BEE NESTING BOX

[76] Inventor: Fred J. Pederson, P.O. Box 415, Ambrose, N. Dak. 58833

[21] Appl. No.: 698,093

[22] Filed: Feb. 4, 1985

[51] Int. Cl.⁴ ............................................. A01K 47/00
[52] U.S. Cl. .................................................. 6/1; 6/11
[58] Field of Search ........................................ 6/1, 11

[56] References Cited

U.S. PATENT DOCUMENTS

| 1,426,551 | 8/1922 | Cress | 6/11 |
| 1,830,592 | 11/1931 | Coddington | 6/11 |
| 3,191,199 | 6/1965 | Barnes, Jr. | 6/11 |
| 3,231,907 | 2/1966 | Covington | 6/1 |
| 4,207,637 | 6/1980 | Niebur | 6/1 |
| 4,257,134 | 3/1981 | Niebur | 6/1 |
| 4,319,371 | 3/1982 | Wiederrich | 6/1 |

Primary Examiner—Hugh R. Chamblee
Attorney, Agent, or Firm—Zarley, McKee, Thomte, Voorhees & Sease

[57] ABSTRACT

A leafcutter bee nesting box is formed from a mixture of sawdust and shredded paper such as newspaper or the like. A slurry formed of the sawdust, paper and water is placed into the mold box and subsequently removed therefrom with the resulting box having approximately 1100 cylindrical bee tunnels formed therein which extend between the front and back portions of the nesting box.

4 Claims, 9 Drawing Figures

BEE NESTING BOX

BACKGROUND OF THE INVENTION

This invention relates to a bee nesting box and more particularly to a leafcutter bee nesting box. Leafcutter bees are widely used in the United States and Canada to cross-pollinate alfalfa plants to ensure seed production. Leafcutter bee growers normally use a nesting box which is filled with bee larvae and then transported to bee buyers who then incubate and hatch the bee larvae, or they can sell just the cocoons after they have been extracted from the box. After the larvae have hatched, the growers normally desire to dispose of the nesting box to prevent parasites and diseases from spreading to clean bee growing areas. If the boxes are not disposable, the next hatch of bees could be in infested with parasites and subjected to disease transmitted by the nesting boxes.

It is therefore a principal object of the invention to provide a disposable leafcutter bee nesting box.

A further object of the invention is to provide a bee nesting box which is economical of manufacture.

Still another object of the invention is to provide a bee nesting box which is designed to prevent parasites from boring from one bee tunnel to another.

Still another object of the invention is to provide a bee nesting box designed to prevent parasites from boring into the outermost bee tunnels formed therein.

Still another object of the invention is to provide a bee nesting box comprised of sawdust and shredded paper so that the box may be disposed of by incineration.

Yet another object of the invention is to provide a bee nesting box comprised of sawdust and paper so that the box will "breathe".

Still another object of the invention is to provide a bee nesting box wherein the bee tunnels are cylindrical which aids in parasite prevention.

Still another object of the invention is to provide a bee nesting box comprised of a wood material.

Still another object of the invention is to provide a leafcutter bee nesting box which is lightweight.

Yet another object of the invention is to provide a method of manufacturing a bee nesting box and to provide the necessary apparatus for producing the bee nesting box of this invention.

These and other objects will be apparent to those skilled in the art.

SUMMARY OF THE INVENTION

Figure 1:
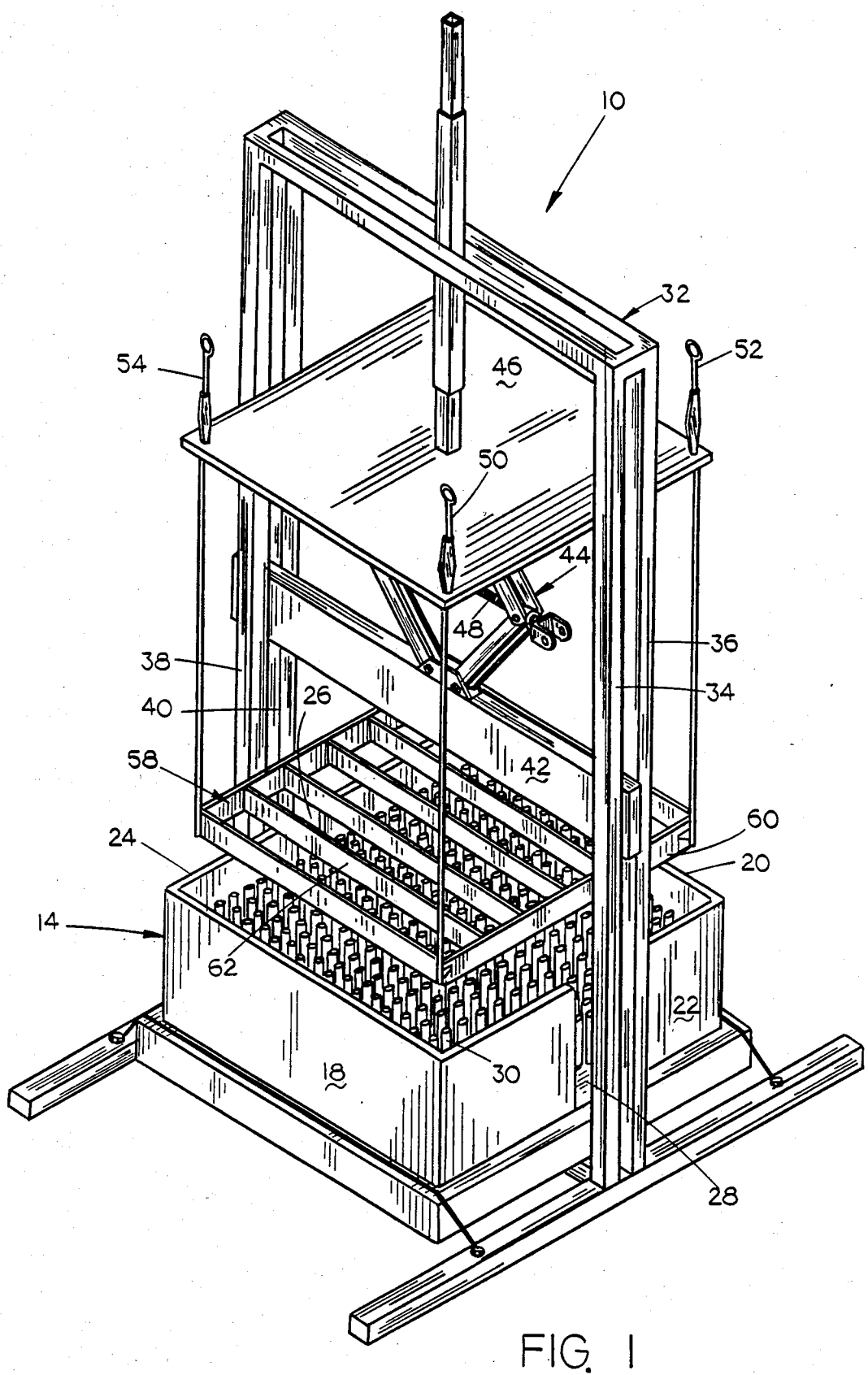
FIG. 1 a perspective view of the apparatus for forming the bee nesting box of this invention.
Figure 2:
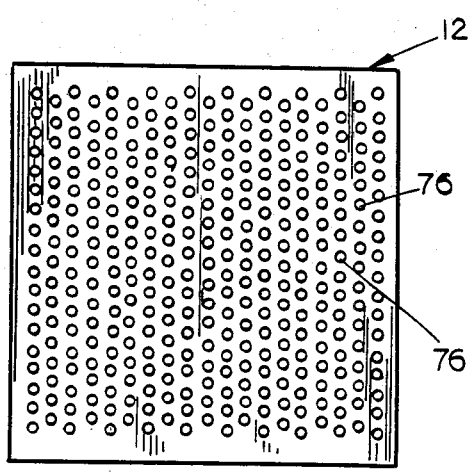
FIG. 2 is a top view of the bee nesting box of this invention.
Figure 4:
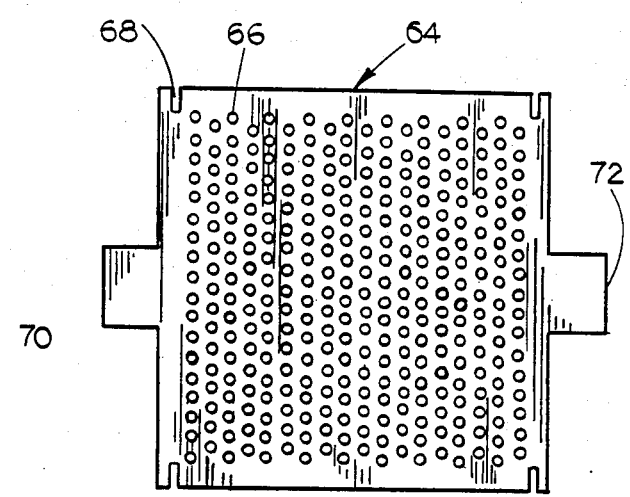
FIG. 4 is a plan view of the box support plate portion of the apparatus of FIG. 1.
Figure 3:
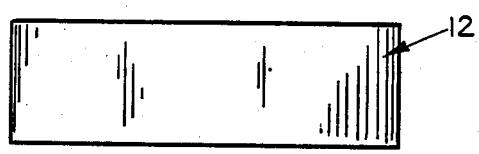
FIG. 3 is a side view of the been nesting box of this invention.
Figure 5:
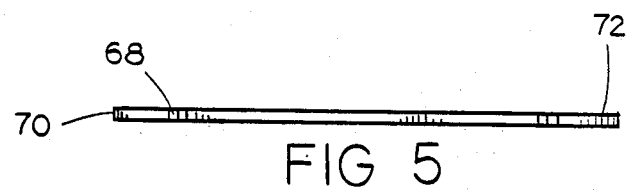
FIG. 5 is a end view of the plate of FIG. 4.
Figure 6:
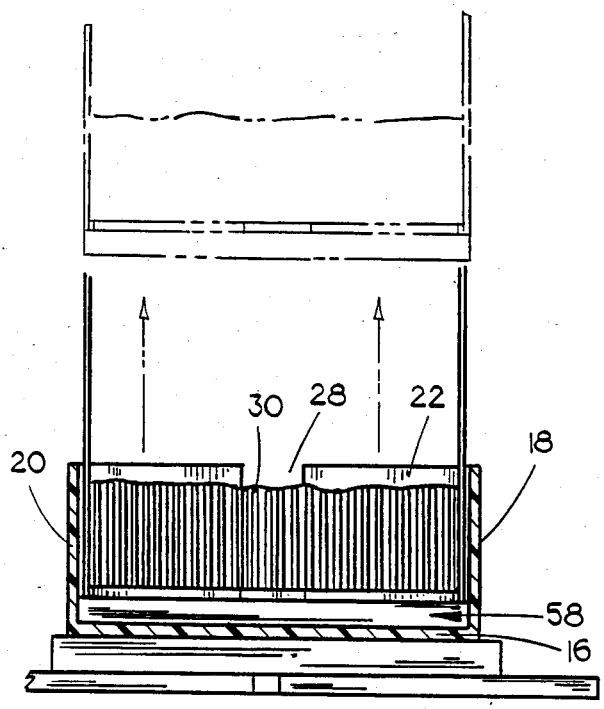
FIGS. 6 and 7 are side views illustrating the sequence of the operation.
Figure 7:
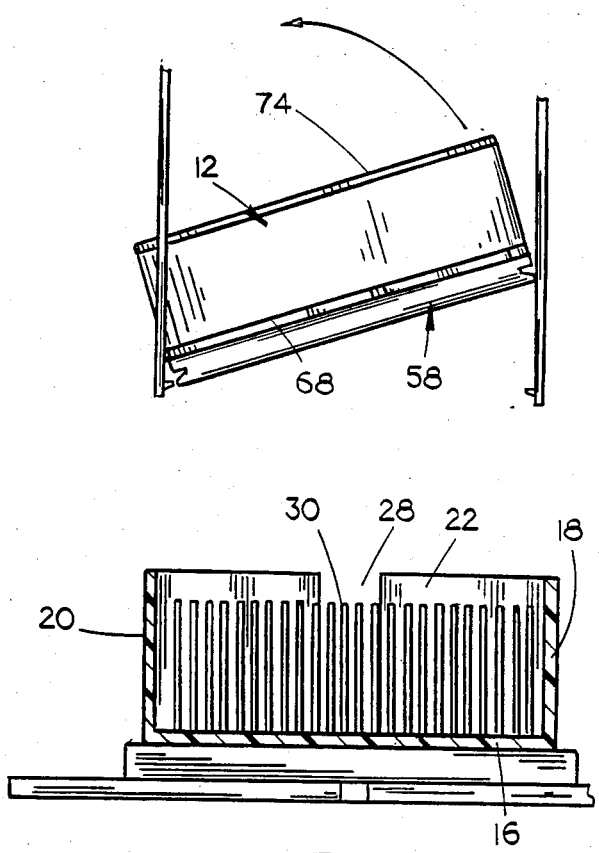
Figure 8:
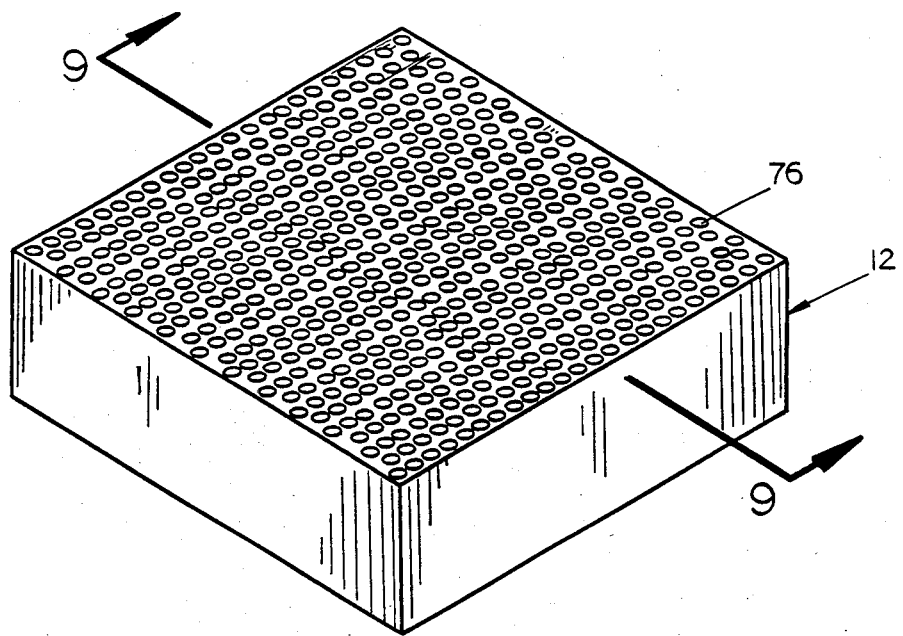
FIG. 8 is a perspective view of the bee nesting box of this invention.
Figure 9:
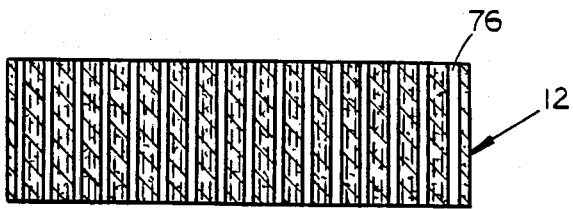
FIG. 9 is a sectional view of the box of this invention as seen on lines 9—9 of FIG. 8.

The bee nesting box of this invention is formed by placing a slurry of sawdust, water and shredded newspaper into a mold box and then removing the nesting box from the mold box and permitting the same to dry. The bee nesting box of this invention is essentially a block member having a back portion, a front portion, a top edge, a bottom edge, and opposite side edges. A plurality of spaced-apart cylindrical bee tunnels are formed in the block member which extend between the front and back portions of the block member. The bee tunnels are spaced-apart approximately ⅛ inch to prevent parasites from boring from one bee tunnel to another. The outermost bee tunnels are also spaced inwardly from the edges of the block member to prevent parasites from boring into the tunnels.

DESCRIPTION OF THE PREFERRED EMBODIMENT

The numeral 10 refers generally to the apparatus for producing the nesting box 12 of this invention. Apparatus 10 includes a mold box 14 having a bottom 16, upstanding sides 18, 20, 22 and 24. As seen in the drawings, sides 22 and 24 are provided with elongated slots or openings 26 and 28 formed therein respectively. Preferably mold box 14 is formed of a plexiglass material with the bottom 16 being also comprised of a plexiglass material with approximately 1089 15/64 diameter holes that are fitted with 15/64 diameter nylon dowels 30 extending upwardly therefrom. Preferably, the dowels 30 are approximately 7¾ inches long. The inside dimensions of the box 14 are preferably 13½ inches by 13½ inches. The method of this invention which is described in more detail hereinafter result in approximately a four percent shrinkage so that the bee tunnels in the box 12 are approximately 7/32 inches in diameter with the outside of the box 12 being approximately 13 inches by 13 inches.

A frame means 32 is provided and includes a pair of upstanding posts 34, 36 and 38, 40 at opposite sides of the mold box 14 as seen in the drawings. Frame member 42 is secured to the posts 34, 36 and 38, 40 and extends therebetween above box 14 and has the lower end of an automobile screw jack 44 mounted thereon. The upper end of jack 44 has a horizontally disposed flat plate 46 mounted thereon for movement therewith. Screw jack 44 includes a conventional threaded rod 48 for raising and lowering the jack and the plate 46.

Rods 50, 52, 54 and 56 (not shown) are secured to the plate 46 adjacent the corners thereof for movement therewith and extend downwardly therefrom as illustrated in the drawings. A metal grid 58 is selectively removably secured to the lower ends of the rods 50, 52, 54 and 56 for movement therewith and includes a peripheral frame portion 60 having a plurality of bars 62 secured thereto and extending thereacross. Frame 60 is designed so that it will fit within the mold box 14 between the outermost dowels 30 and the inside surfaces of the walls of the mold box 14. The bars 62 are designed to be received between the dowels 30. When metal grid 58 is in its lowermost position, the bottom of grid 58 rests on the upper surface of bottom 16 of mold box 14.

The numeral 64 refers to a box support plate which is removably mounted on the metal grid 58. Plate 64 is provided with a plurality of openings 66 formed therein adapted to receive the dowels 30 extending therethrough. Support plate 64 is provided with notches 68 formed in the periphery thereof adapted to removably receive the rods 50, 52, 54 and 56. Plate 64 is also provided with a pair of laterally extending handle portions 70 and 72. Preferably, plate 64 is formed of a plexiglass material and has a thickness of approximately ¾ inch.

In operation, plate 64 is initially positioned on metal grid 58 with the notches 68 receiving the rods 50, 52, 54 and 56. Jack 44 is then actuated to lower plate 46 which causes the grid 58 and the plate 64 to be lowered downwardly into the interior of mold box 14 until the grid 58 rests on bottom 16 of mold box 14. Thin flat sheets of plastic or the like are then placed on the inside of the mold box 14 inwardly of the openings 26 and 28 to prevent the slurry from passing outwardly therethrough. A slurry comprised of a mixture of sawdust, shredded paper such as newspaper and water is then placed in the mold box 14. The proportions of the sawdust and newspaper will vary with more paper being utilized if additional strength is desired. For example, a typical slurry mixture would be comprised of 2-3 pounds sawdust, 4-6 sheets of shrerdded newspaper, and 2-3 gallons water. The slurry is placed in the mold box 14 until only the upper ends of the dowels 30 are exposed. Jack 44 is then actuated to raise plate 46 relative to the frame means 32 which causes the metal grid 58 and the plate 64 to be raised thereby pulling the box 12 from the mold box 14. When plate 64 has been raised above the upper ends of the dowels 30, a plate 74 is positioned on the top of the molded slurry. Grid 58 is then detached from rods 50, 52, 54 and 56 and plate 74, molded slurry, grid 58 and plate 64 are then removed from the apparatus, inverted and placed on a drying rack. Plate 64 and gird 58 are then removed and grid 58 repositioned on the rods 52, 54, 56 and 58 so that the molding process may be repeated.

The resulting box 12 results in a plurality of cylindrical bee tunnels 76 being formed which extend between the back and front sides of the box 12. When the box 12 is removed from the mold, the tunnels 76 extend completely through the box 12. However, a thin (at least ⅛") layer of slurry is applied to the back of the box 12 to seal the tunnels so that only the front side of the box 12 has open tunnels. As seen in the drawings, the outermost bee tunnels 76 are spaced from the edges of the box 12 to prevent parasites from boring into the outermost bee tunnels from the side edges of the box. Further, the tunnels 76 are spaced apart approximately ⅛ inch to prevent parasites from boring from one bee tunnel to another.

The resulting box 12 is lightweight and is sufficiently porous so that the box will "breathe" to prevent the formation of mold or the like which could be devastating to the bee larvae. The bees make cocoons and lay eggs in the tunnels of the nesting box while the box is in the alfalfa field during the growing season. The box may then be shipped to a buyer for subsequent incubation and hatching. When the bees have hatched and have left the box 12, the box 12 may be crumbled and burned thereby preventing the spread of disease and parasites. The fact that the boxes are formed from inexpensive materials permits the boxes to be disposed of without great expense being incurred.

Thus it can be seen that the box of this invention accomplishes at least all of its stated objectives.

I claim:

1. A bee nesting box, comprising,
   a quadrilateral-shaped member having a front portion, a back portion, a top edge, a bottom edge, and opposite side edges,
   said member having a plurality of horizontally disposed and spaced-apart cylindrical bee tunnels formed therein extending between said front and back portions,
   the outermost of said tunnels being spaced from top edge, bottom edge and opposite edges to provide a parasite barrier between said edges and said tunnels,
   each of said tunnels being spaced approximately one-eighth inch apart to prevent parasites from boring from one tunnel to another,
   said member being formed from a single molded piece of a lightweight fibrous and breathable material.

2. The box of claim 1 wherein said fibrous material is a mixture of sawdust and shredded paper.

3. The box of claim 1 wherein said fibrous material is ground straw.

4. The box of claim 1 wherein said bee tunels are sealed at said back portion.

* * * * *